(12) United States Patent
Bruneau et al.

(10) Patent No.: US 7,691,130 B2
(45) Date of Patent: Apr. 6, 2010

(54) SPINAL IMPLANTS INCLUDING A SENSOR AND METHODS OF USE

(75) Inventors: Aurelien Bruneau, Memphis, TN (US); Eric C. Lange, Collierville, TN (US); Kent M. Anderson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 482 days.

(21) Appl. No.: 11/340,974

(22) Filed: Jan. 27, 2006

(65) Prior Publication Data

US 2007/0191833 A1    Aug. 16, 2007

(51) Int. Cl.
*A61B 17/70* (2006.01)
(52) U.S. Cl. ..................................... 606/249
(58) Field of Classification Search ............... 600/594; 623/17.11–17.16; 606/90, 248, 279, 24
See application file for complete search history.

(56) References Cited

U.S. PATENT DOCUMENTS

| | | | |
|---|---|---|---|
| 2,677,369 | A | 5/1954 | Knowles |
| 3,648,691 | A | 3/1972 | Lumb et al. |
| 4,011,602 | A | 3/1977 | Rybicki et al. |
| 4,066,082 | A | 1/1978 | Arcan et al. |
| 4,257,409 | A | 3/1981 | Bacal et al. |
| 4,554,914 | A | 11/1985 | Kapp et al. |
| 4,566,466 | A | 1/1986 | Ripple et al. |
| 4,573,454 | A | 3/1986 | Hoffman |
| 4,604,995 | A | 8/1986 | Stephens et al. |
| 4,611,582 | A | 9/1986 | Duff |
| 4,657,550 | A | 4/1987 | Daher |
| 4,686,970 | A | 8/1987 | Dove et al. |
| 4,827,918 | A | 5/1989 | Olerud |

(Continued)

FOREIGN PATENT DOCUMENTS

DE    2821678 A1    11/1979

(Continued)

OTHER PUBLICATIONS

"Dispositivo Intervertebrale Ammortizzante DIAM," date unknown, p. 1.

(Continued)

*Primary Examiner*—Eduardo C Robert
*Assistant Examiner*—Ellen C Hammond
(74) *Attorney, Agent, or Firm*—Coats and Bennett, P.L.L.C.

(57) ABSTRACT

A method of spacing spinal elements includes installing a first spinal implant having a sensor associated therewith; selecting a second spinal implant based on measurement data provided by the sensor; and replacing the first spinal implant with the second spinal implant. The first and second implants may be installed in separate surgical procedures, or during the same surgical procedure, and the implants may be positioned between a superior spinous process and an inferior spinous process and advantageously directly engage the same. The selection of the second implant may be based on the data provided by the sensor and a material property of the second spinal implant, such as its stiffness. The measurement data may correspond to strain or force data. The sensor may be, but is not required to be, embedded in the first spinal implant. A corresponding apparatus is described.

17 Claims, 4 Drawing Sheets

U.S. PATENT DOCUMENTS

| | | |
|---|---|---|
| 4,863,476 A | 9/1989 | Shepperd |
| 4,931,055 A | 6/1990 | Bumpus et al. |
| 5,011,484 A | 4/1991 | Bréard |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,219,349 A | 6/1993 | Krag et al. |
| 5,306,275 A | 4/1994 | Bryan |
| 5,360,016 A | 11/1994 | Kovacevic |
| 5,360,430 A | 11/1994 | Lin |
| 5,366,455 A | 11/1994 | Dove |
| 5,390,683 A | 2/1995 | Pisharodi |
| 5,395,370 A | 3/1995 | Muller et al. |
| 5,415,661 A | 5/1995 | Holmes |
| 5,437,672 A | 8/1995 | Alleyne |
| 5,445,008 A * | 8/1995 | Wachter et al. ............ 73/24.06 |
| 5,454,812 A | 10/1995 | Lin |
| 5,456,724 A | 10/1995 | Yen et al. |
| 5,496,318 A | 3/1996 | Howland et al. |
| 5,518,498 A | 5/1996 | Lindenberg et al. |
| 5,545,229 A * | 8/1996 | Parsons et al. ........... 623/17.15 |
| 5,554,191 A | 9/1996 | Lahille et al. |
| 5,609,634 A | 3/1997 | Voydeville |
| 5,609,635 A | 3/1997 | Michelson |
| 5,628,756 A | 5/1997 | Barker, Jr. et al. |
| 5,645,599 A | 7/1997 | Samani |
| 5,665,122 A | 9/1997 | Kambin |
| 5,672,175 A | 9/1997 | Martin |
| 5,674,295 A | 10/1997 | Ray et al. |
| 5,676,702 A | 10/1997 | Ratron |
| 5,690,649 A | 11/1997 | Li |
| 5,702,455 A | 12/1997 | Saggar |
| 5,704,937 A | 1/1998 | Martin |
| 5,707,390 A | 1/1998 | Bonutti |
| 5,716,416 A | 2/1998 | Lin |
| 5,719,324 A * | 2/1998 | Thundat et al. ............ 73/24.01 |
| 5,810,815 A | 9/1998 | Morales |
| 5,836,948 A | 11/1998 | Zucherman et al. |
| 5,860,977 A | 1/1999 | Zucherman et al. |
| 5,976,186 A | 11/1999 | Bao et al. |
| 5,989,334 A | 11/1999 | Dry |
| 6,016,686 A * | 1/2000 | Thundat ..................... 73/23.2 |
| 6,022,376 A | 2/2000 | Assell et al. |
| 6,048,342 A | 4/2000 | Zucherman et al. |
| 6,050,722 A * | 4/2000 | Thundat et al. ............ 374/121 |
| 6,068,630 A | 5/2000 | Zucherman et al. |
| 6,096,559 A * | 8/2000 | Thundat et al. ............ 436/147 |
| 6,113,639 A * | 9/2000 | Ray et al. ................ 623/17.16 |
| 6,118,124 A * | 9/2000 | Thundat et al. ............ 250/332 |
| 6,126,689 A | 10/2000 | Brett |
| 6,127,597 A | 10/2000 | Beyar et al. |
| 6,132,464 A | 10/2000 | Martin |
| 6,167,748 B1 * | 1/2001 | Britton et al. .............. 73/24.06 |
| 6,190,414 B1 | 2/2001 | Young |
| 6,212,939 B1 * | 4/2001 | Thundat ..................... 73/24.02 |
| 6,214,050 B1 | 4/2001 | Huene |
| 6,263,736 B1 * | 7/2001 | Thundat et al. ......... 73/514.36 |
| 6,289,717 B1 * | 9/2001 | Thundat et al. .............. 73/23.2 |
| 6,293,949 B1 | 9/2001 | Justis et al. |
| 6,311,549 B1 * | 11/2001 | Thundat et al. ............ 73/54.24 |
| 6,311,557 B1 * | 11/2001 | Davis et al. ............. 73/514.31 |
| 6,336,366 B1 * | 1/2002 | Thundat et al. ......... 73/514.34 |
| 6,340,363 B1 | 1/2002 | Bolger et al. |
| 6,352,524 B1 * | 3/2002 | Bunt et al. .................. 604/285 |
| 6,352,537 B1 | 3/2002 | Strnad |
| 6,364,883 B1 | 4/2002 | Santilli |
| 6,375,682 B1 | 4/2002 | Fleischmann et al. |
| 6,395,033 B1 | 5/2002 | Pepper |
| 6,402,750 B1 | 6/2002 | Atkinson et al. |
| 6,419,704 B1 | 7/2002 | Ferree |
| 6,436,346 B1 * | 8/2002 | Doktycz et al. ................ 422/51 |
| 6,440,169 B1 | 8/2002 | Elberg et al. |
| 6,447,448 B1 * | 9/2002 | Ishikawa et al. ............ 600/300 |
| 6,451,019 B1 | 9/2002 | Zucherman et al. |
| 6,475,639 B2 * | 11/2002 | Shahinpoor et al. ......... 428/614 |
| 6,515,593 B1 | 2/2003 | Stark et al. |
| 6,520,991 B2 | 2/2003 | Huene |
| 6,539,947 B2 | 4/2003 | Boies et al. |
| 6,554,833 B2 | 4/2003 | Levy |
| 6,576,016 B1 | 6/2003 | Hochshuler et al. |
| 6,582,433 B2 | 6/2003 | Yun |
| 6,582,467 B1 | 6/2003 | Teitelbaum et al. |
| 6,626,944 B1 * | 9/2003 | Taylor ..................... 623/17.16 |
| 6,645,207 B2 | 11/2003 | Dixon et al. |
| 6,652,534 B2 | 11/2003 | Zucherman et al. |
| 6,685,742 B1 | 2/2004 | Jackson |
| 6,695,842 B2 | 2/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,534 B2 | 5/2004 | Sherman |
| 6,736,818 B2 | 5/2004 | Perren et al. |
| 6,758,863 B2 | 7/2004 | Estes et al. |
| 6,761,720 B1 | 7/2004 | Senegas |
| 6,835,205 B2 | 12/2004 | Atkinson et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,037,438 B2 * | 5/2006 | Benzel et al. .................. 216/2 |
| 7,041,136 B2 | 5/2006 | Goble et al. |
| 7,048,736 B2 | 5/2006 | Robinson et al. |
| 7,081,120 B2 | 7/2006 | Li et al. |
| 7,087,083 B2 | 8/2006 | Pasquet et al. |
| 7,097,648 B1 | 8/2006 | Globerman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,442,208 B2 | 10/2008 | Mathieu et al. |
| 7,445,637 B2 | 11/2008 | Taylor |
| 2001/0028036 A1 * | 10/2001 | Thundat et al. ......... 250/339.02 |
| 2002/0006682 A1 * | 1/2002 | Benzel et al. .................. 438/50 |
| 2002/0039620 A1 * | 4/2002 | Shahinpoor et al. ........ 427/2.12 |
| 2002/0139171 A1 * | 10/2002 | Benzel et al. .............. 73/29.01 |
| 2002/0143331 A1 | 10/2002 | Zucherman et al. |
| 2002/0174724 A1 * | 11/2002 | Benzel et al. ................. 73/763 |
| 2003/0062579 A1 * | 4/2003 | Benzel et al. ................. 257/419 |
| 2003/0116813 A1 * | 6/2003 | Benzel et al. ................. 257/414 |
| 2003/0153915 A1 | 8/2003 | Nekozuka et al. |
| 2003/0236472 A1 | 12/2003 | Van Hoeck et al. |
| 2004/0021184 A1 * | 2/2004 | Benzel et al. ................. 257/414 |
| 2004/0097931 A1 | 5/2004 | Mitchell |
| 2004/0133204 A1 | 7/2004 | Davies |
| 2004/0167625 A1 | 8/2004 | Beyar et al. |
| 2004/0204647 A1 | 10/2004 | Grupp et al. |
| 2004/0260397 A1 | 12/2004 | Lambrecht et al. |
| 2005/0010293 A1 | 1/2005 | Zucherman et al. |
| 2005/0049708 A1 | 3/2005 | Atkinson et al. |
| 2005/0165398 A1 | 7/2005 | Reiley |
| 2005/0203512 A1 | 9/2005 | Hawkins et al. |
| 2005/0203624 A1 | 9/2005 | Serhan et al. |
| 2005/0228391 A1 | 10/2005 | Levy et al. |
| 2005/0234555 A1 * | 10/2005 | Sutton et al. ............. 623/17.15 |
| 2005/0261768 A1 | 11/2005 | Trieu |
| 2005/0273170 A1 * | 12/2005 | Navarro et al. ........... 623/17.13 |
| 2005/0288672 A1 | 12/2005 | Feree |
| 2006/0004447 A1 | 1/2006 | Mastrorio et al. |
| 2006/0004455 A1 | 1/2006 | Leonard et al. |
| 2006/0015181 A1 | 1/2006 | Elberg |

| | | | |
|---|---|---|---|
| 2006/0064165 A1 | 3/2006 | Zucherman et al. | |
| 2006/0084983 A1 | 4/2006 | Kim | |
| 2006/0084985 A1 | 4/2006 | Kim | |
| 2006/0084987 A1 | 4/2006 | Kim | |
| 2006/0084988 A1 | 4/2006 | Kim | |
| 2006/0085069 A1 | 4/2006 | Kim | |
| 2006/0089654 A1 | 4/2006 | Lins et al. | |
| 2006/0089719 A1 | 4/2006 | Trieu | |
| 2006/0106381 A1 | 5/2006 | Ferree et al. | |
| 2006/0106397 A1 | 5/2006 | Lins | |
| 2006/0111728 A1 | 5/2006 | Abdou | |
| 2006/0116690 A1 | 6/2006 | Pagano | |
| 2006/0122620 A1 | 6/2006 | Kim | |
| 2006/0136060 A1 | 6/2006 | Taylor | |
| 2006/0136061 A1* | 6/2006 | Navarro et al. | 623/17.13 |
| 2006/0184247 A1 | 8/2006 | Edidin et al. | |
| 2006/0184248 A1 | 8/2006 | Edidin et al. | |
| 2006/0195102 A1 | 8/2006 | Malandain | |
| 2006/0217726 A1 | 9/2006 | Maxy et al. | |
| 2006/0264938 A1 | 11/2006 | Zucherman et al. | |
| 2006/0271044 A1 | 11/2006 | Petrini et al. | |
| 2006/0293662 A1 | 12/2006 | Boyer, II et al. | |
| 2007/0073292 A1* | 3/2007 | Kohm et al. | 606/61 |
| 2007/0151116 A1 | 7/2007 | Malandain | |
| 2007/0282443 A1 | 12/2007 | Globerman et al. | |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1138268 A1 | 10/2001 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2816197 A1 | 5/2002 |
| JP | 02-224660 | 9/1990 |
| JP | 09-075381 | 3/1997 |
| SU | 988281 | 1/1983 |
| WO | WO 94/26192 | 11/1994 |
| WO | WO 94/26195 | 11/1994 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | 03045262 A2 | 6/2003 |
| WO | WO 03/057055 A1 | 7/2003 |
| WO | 2004005872 A2 | 1/2004 |
| WO | WO 2004/047689 A1 | 6/2004 |
| WO | WO 2004/047691 A1 | 6/2004 |
| WO | 2004084768 A2 | 10/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | 2005120203 A2 | 12/2005 |
| WO | 2006089085 A2 | 8/2006 |
| WO | WO 2007/034516 A1 | 3/2007 |

OTHER PUBLICATIONS

"Tecnica Operatoria Per II Posizionannento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, ppp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192- S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerative del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative á la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopéclique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer lnnotec, "DIAM—Modified CAD Geometry and Meshing," date unknown.

Taylor et al., "Analyse d'une experience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

* cited by examiner

SPINAL IMPLANTS INCLUDING A SENSOR AND METHODS OF USE

BACKGROUND

The present application is directed generally to spinal implants, such as interspinous implants, and more particularly to spinal implants having a sensor associated therewith and methods of using the sensor.

The spine includes a number of vertebral members that are typically vertically spaced apart by intervertebral discs. This arrangement permits the spine to undergo slight flexion, extension, lateral flexion, and rotation. In addition, the vertebrae typically include bony protrusions, called spinous processes, that extend posteriorly from the spinal axis.

Various medical procedures include spacing apart the vertebral members that extend along a section of the spine. These procedures may be required due to damage to one or more of the vertebral members and/or intervertebral discs caused by a specific traumatic event, a degenerative condition, a tumor, infection, or the like. These procedures typically involve decompressing the relevant vertebral members and installing some form of spinal implant. For example, a bone plate may be secured to adjacent vertebral members to fix their relative positions. However, many procedures call for the vertebral members to remain moveable relative to each other, at least to some extent. For example, a spacer may be inserted between adjacent spinous processes, or other vertebral elements, to provide elastic resistance to relative compression between the elements. The mechanical properties of the-spacer (e.g., its size and stiffness) help determine how and to what extent the spacer stabilizes the spinal column. As such, it may be desirable to determine target mechanical properties for the spacer, which is not always possible to predict a priori with the desired level of accuracy.

SUMMARY

In one illustrative embodiment, the present application provides a method of spacing spinal elements comprising: installing a first spinal implant having a sensor associated therewith; selecting a second spinal implant based on measurement data provided by the sensor; and replacing the first spinal implant with the second spinal implant. The first and second implants may be installed in separate surgical procedures, or during the same surgical procedure, and the implants may be positioned between a superior spinous process and an inferior spinous process and advantageously directly engage the same. The selection of the second implant may be based on the data provided by the sensor and a material property of the second spinal implant, such as its stiffness. The measurement data may correspond to strain or force data. The sensor may be, but is not required to be, embedded in the first spinal implant, such as in a removable module. A corresponding apparatus is described.

DETAILED DESCRIPTION

In one embodiment, the present application relates to an interspinous implant 20 that has an associated sensor 30. See FIG. 1. Such an implant 20 may be used to space a superior spinous process 12 from an inferior spinous process 14 in adjacent vertebrae 10. See FIG. 2. The implant 20 may be put in place temporarily in order to obtain measurement data, and may therefore be sometimes referred to herein as a test implant 20.

Figure 1:
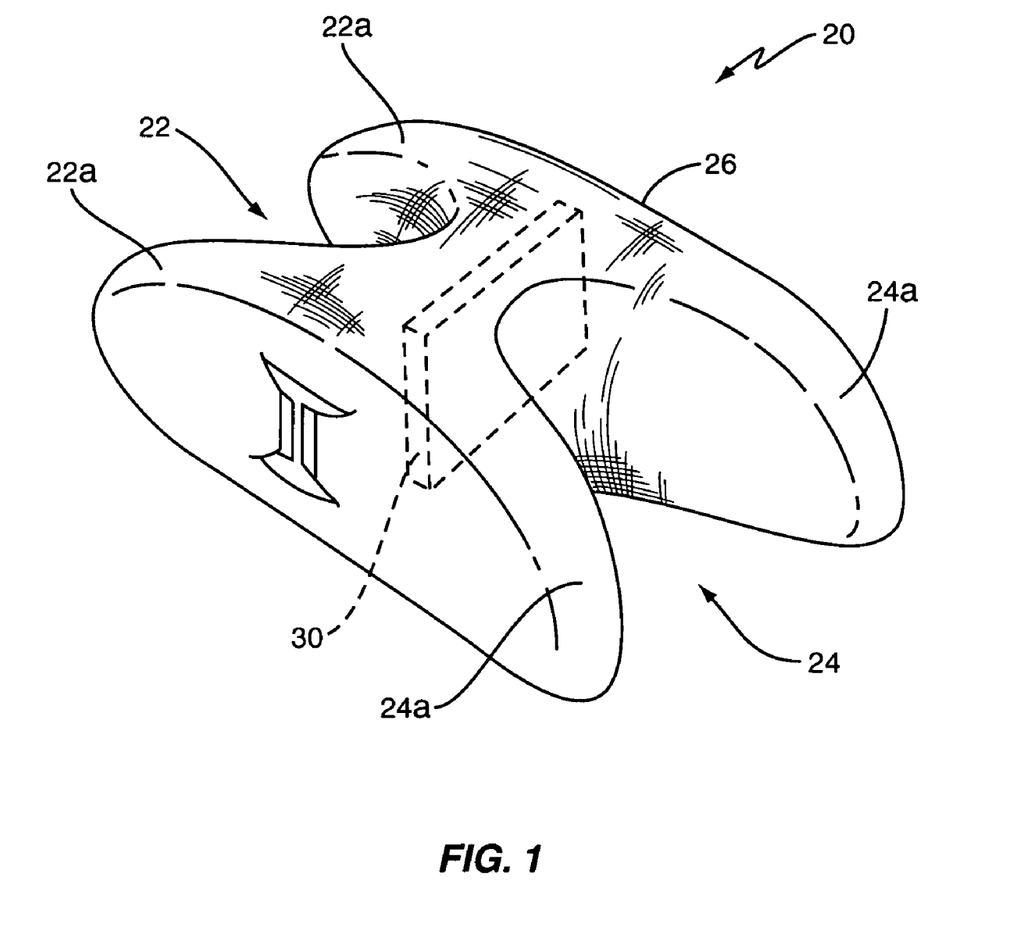
FIG. 1 shows a spinal implant in accordance with one embodiment.

The implant 20, sometimes referred to as a spacer, typically includes a superior saddle 22, an inferior saddle 24, and a midsection 26 therebetween. The superior and inferior saddles 22,24 are formed by respective lugs 22a,24a extending from the midsection 26, and are configured to receive the superior and inferior spinous processes 12,14, respectively. The saddles 22,24 may be symmetric or asymmetric, as is desired. The midsection 26 is intended to substantially fill the space between the spinous processes 12,14, and is advantageously flexible and elastic. For additional information, attention is directed to U.S. Pat. No. 6,626,944 to Taylor, which is incorporated herein by reference.

A sensor 30 is associated with the implant 20. The sensor 30, in one embodiment, may take the form of a conventional strain gage. Such a strain gage 30 should be oriented to measure vertical strain on the implant 20 between the spinous processes 12,14; however, the sensor 30 may alternatively or additionally measure strains in other directions. In various alternative embodiments, the sensor 30 measures load, pressure, stress, strain, vibration frequency, and the like, either at a moment in time, or over time. The sensor 30 may advantageously be disposed in the midsection 26 of the implant 20, such as embedded therein, although this is not required.

It is intended that the sensor 30 will generate measurement data about the implant 20 and/or its mechanical environment. Typically, this measurement data is indicative of the forces acting on the implant 20 and/or the resulting strain of the implant 20. This measurement data may be transmitted from the implant using a suitable analog or digital transmitter, which may use radio frequency, thermodynamic, capacitance, or other means to convey the data signal. Alternatively, the measurement data may be supplied via suitable wires or other transmission media to a computer or other measurement data gathering station. The measurement data may be collected from the implant 20 while the implant is in the body, or after the implant 20 is removed from the body.

Figure 2:
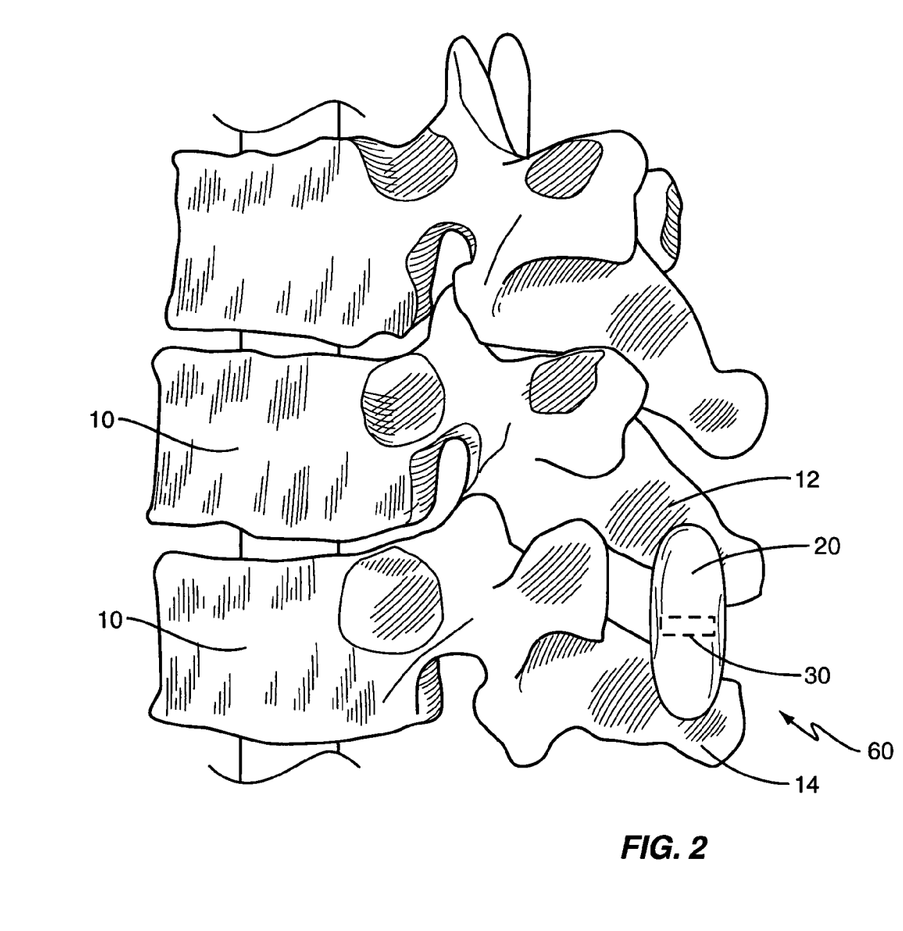
FIG. 2 shows a portion of a spine with an installed sensor-equipped test spinal implant.
Figure 3:
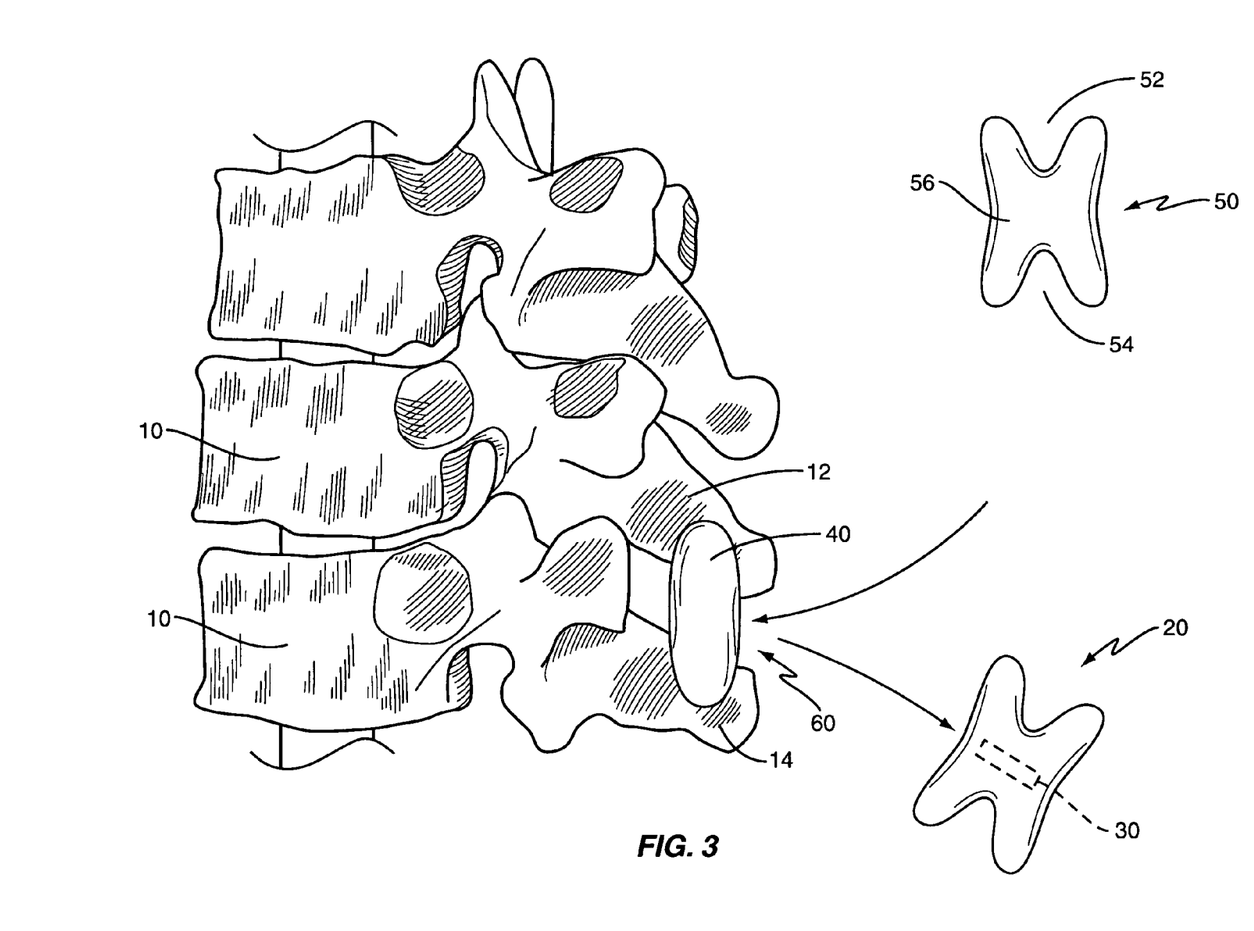
FIG. 3 shows a portion of a spine with an installed long-term spinal implant replacing the sensor-equipped test spinal implant.

The sensor-equipped test implant 20 may be inserted between the superior and inferior spinous processes 12,14 of adjacent vertebrae 10 during a surgical procedure. The surgical procedure may be similar to that used for the product sold under the trade name DIAM Spinal Stabilization System, available from Medtronic Sofamor Danek, Inc. of Memphis, Tenn. Post-operatively, the implant's sensor 30 generates measurement data as discussed above. This data is reviewed and used to help select a second implant 40 which replaces the first implant 20 via a second surgical procedure. More particularly, a plurality of candidate implants, such as implants 40,50, may be provided with differing material properties. Like implant 20, the candidate implants 40,50 have respective superior saddles 42,52, inferior saddles 44,54, and midsections 46,56; but, unlike implant 20, the candidate implants 40,50 advantageously do not include associated sensors. Based on the measurement data from sensor 30, one of the candidate implants 40,50 is chosen so that its material properties will be appropriate for the situation. For example, based on the measurement data, a doctor may conclude that a spacer between the spinous processes 12,14 should have a certain overall stiffness. The candidate spacer implants 40,50 may have a variety of stiffness levels, indicated in the drawings as stiffness #1 and stiffness #2. One of the available stiffness levels should correspond with the desired stiffness identified by the doctor, and the corresponding candidate spacer implant (e.g., candidate implant 40) is chosen. Then, the first implant 20 is removed and replaced with the chosen implant 40 during a second surgical procedure. Thus, the chosen implant 40 is used to create a spinal stabilizer 60 between the spinous processes 12,14 that helps space the two spinous processes 12,14 apart. It is intended that the spinal stabilizer 60 formed thereby will be in place long-term; as such, the replacement implant may be conceptually thought of as a long-term implant 40. The long-term implant 40 may, in some embodiments, be secured in place using tethers, as disclosed in U.S. Pat. No. 6,626,944.

Figure 4:
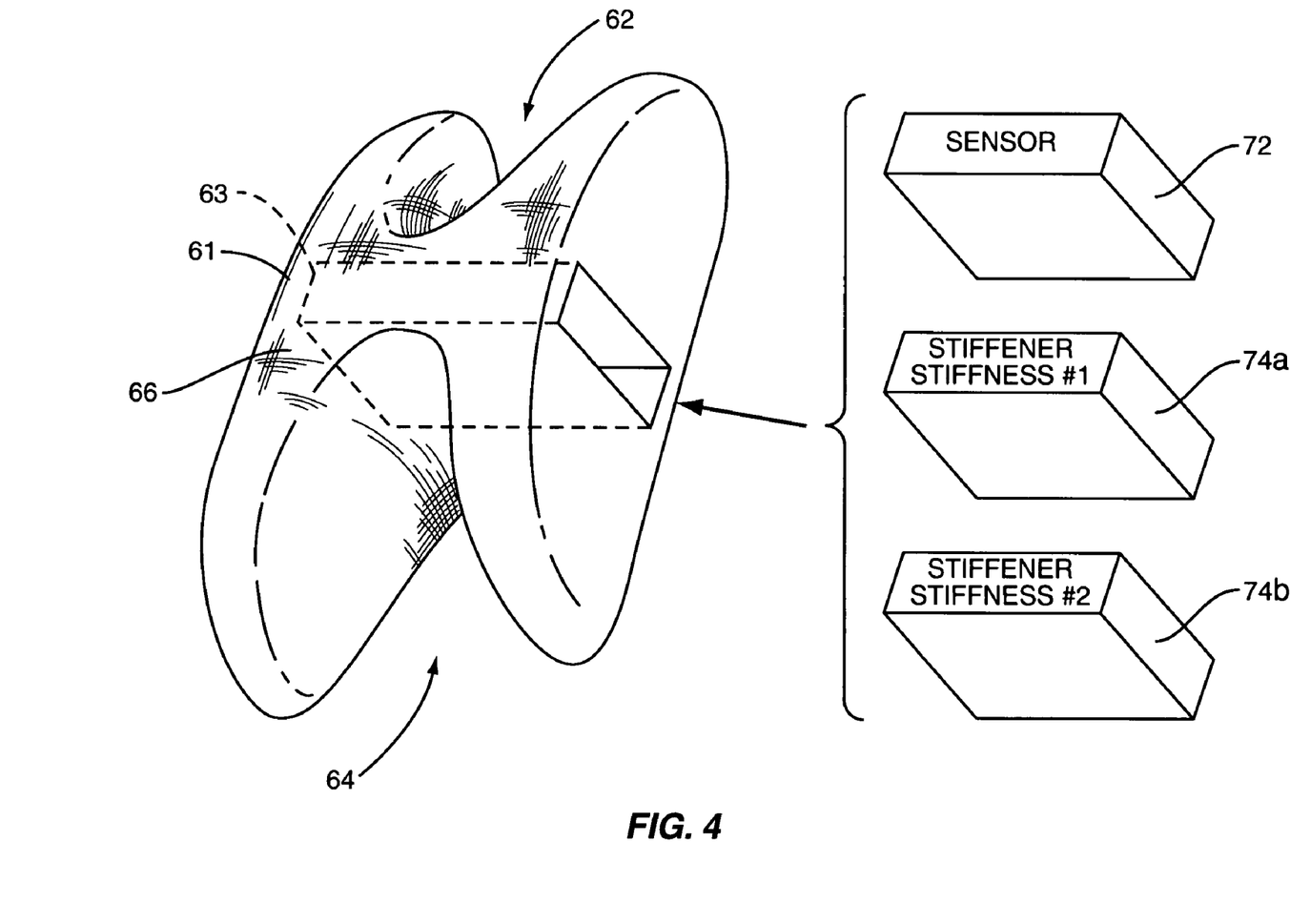
FIG. 4 shows alternative embodiments of the spinal implants using a common receiver body and multiple modular inserts.

In another embodiment, various implants 20,40,50 may be formed of a common receiver body 61 in combination with various modular inserts 72,74a,74b. See FIG. 4. The receiver body 61 may include a superior saddle 62, and an inferior saddle 64. The various inserts 72,74a,74b may be joined to the receiver body 61 and be disposed between the saddles 62,64, such as in a corresponding bay 63 within midsection 66. Thus, a sensor-equipped test implant 20 may be formed by inserting sensor module 72, having sensor 30 disposed therein, into receiver body 61. The same receiver body 61 may then be used to form candidate implant 40 by removing the sensor module 72 and inserting a different module 74a, or form candidate implant 50 by inserting module 74b. Advantageously, the modules 74a,74b have differing material properties, such as different stiffness levels.

The discussion above has assumed that the sensor-equipped test implant 20 is replaced by long-term implant 40 or 50 in a second surgical procedure. During the time period between the first and second surgical procedures, the sensor 30 may be used to collect relevant data with the patient in more "real world" circumstances. The interval between surgical procedures may be a few hours to a month or more. However, in some embodiments, the test implant 20 and the long-term implant 40 or 50 may be installed in the same surgical procedure. For example, the test implant 20 may be installed, the patient may be manipulated by the surgeon during the procedure to allow the sensor 30 to generate the relevant measurement data, long-term implant 40 selected based thereon, and test implant 20 replaced by long-term implant 40, all within the same surgical procedure.

It should be noted that the term "material property" as used herein refers to elastic modulus, flexural modulus, flexural strength, stress-strain curve, Young's modulus, hardness, compression strength, dampening or viscous properties, and the like, whether of a homogenous material or of a composite, and excludes physical dimensions.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present embodiments may, of course, be carried out in other specific ways than those herein set forth without departing from the essential characteristics of the application. The present embodiments are, therefore, to be considered in all respects as illustrative and not restrictive, and all changes coming within the meaning and equivalency range of the appended claims are intended to be embraced therein.

What is claimed is:

1. A method of spacing spinal elements, comprising:
   creating a first incision in a human body during a first surgical procedure;
   installing a first spinal implant having a sensor associated therewith during the first surgical procedure;
   closing the first incision;
   generating measurement data, by said sensor, indicative of at least one mechanical property of the spine with said first spinal implant installed;
   selecting a second spinal implant based on said measurement data and a material property of the second spinal implant;
   thereafter, creating a second incision in the human body during a second surgical procedure;
   replacing said first spinal implant with said second spinal implant during the subsequent second surgical procedure; wherein said replacing the first spinal implant with the second spinal implant comprises replacing a first insert with a second insert by removing the first insert from a receiver body and joining a second insert to the receiver body;
   thereafter, closing the second incision.

2. The method of claim 1 further comprising transmitting said measurement data from said sensor prior to said replacing.

3. The method of claim 1 wherein said measurement data corresponds to strain data.

4. The method of claim 1 wherein said sensor is embedded in said first spinal implant.

5. The method of claim 1 wherein said installing said first spinal implant comprises installing said first spinal implant between a superior spinous process and an inferior spinous process.

6. The method of claim 5 wherein said first spinal implant directly engages both of said superior and inferior spinous processes.

7. The method of claim 1:
   wherein said sensor is affixed to said first spinal implant;
   wherein said installing said first spinal implant comprises installing said first spinal implant between a superior spinous process and an inferior spinous process such that said first spinal implant directly engages both of said superior and inferior spinous processes;
   further comprising transmitting said measurement data from said sensor prior to said replacing.

8. A method of spacing spinal elements, comprising:
   installing a receiver body between a superior spinous process and an inferior spinous process;
   installing a first spinal implant having a sensor associated therewith;
   generating measurement data, by said sensor, indicative of at least one mechanical property of the spine with said first spinal implant installed;
   selecting a second spinal implant based on said measurement data;
   replacing said first spinal implant with said second spinal implant;

wherein said installing said first spinal implant comprises joining said first spinal implant to said receiver body; and wherein replacing said first spinal implant with said second spinal implant comprises removing said first spinal implant from said receiver body and joining said second spinal implant to said receiver body.

9. A method of spacing spinal elements, comprising:
installing a first spinal implant having a sensor associated therewith
generating measurement data, by said sensor, indicative of at least one mechanical property of the spine with said first spinal implant installed;
selecting a second spinal implant based on said measurement data;
replacing said first spinal implant with said second spinal implant;
wherein said sensor is embedded in said first spinal implant;
wherein said installing said first spinal implant comprises installing a receiver body between a superior spinous process and an inferior spinous process such that said receiver body directly engages both of said spinous processes, and joining said first spinal implant to said receiver body;
further comprising transmitting said measurement data from said sensor prior to said replacing;
wherein said selecting said second spinal implant comprises selecting said second spinal implant based on said measurement data and a material property of said second spinal implant; and
wherein replacing said first spinal implant with said second spinal implant comprises removing said first spinal implant from said receiver body and joining said second spinal implant to said receiver body.

10. The method of claim 9 wherein said installing said first spinal implant comprises installing said first spinal implant during a first surgical procedure; and wherein said replacing said first spinal implant with said second spinal implant comprises replacing said first spinal implant with said second spinal implant during a subsequent surgical procedure.

11. A method of spacing a superior spinous process relative to an inferior spinous process, comprising:
inserting a first interspinous implant between the spinous processes; said first implant having a sensor associated therewith;
thereafter, generating measurement data indicative of a mechanical environment for said first interspinous implant when installed;
disposing a spinal stabilizer, having a mechanical property based on said measurement data, between the spinous processes;
wherein said first interspinous implant comprises a receiver body having a superior saddle, an inferior saddle, and a compressible body therebetween; said sensor disposed in a sensor module mated to said body;
wherein said inserting a first interspinous implant comprises inserting said first spinal implant between the spinous processes such that said superior and inferior saddles engage the superior and inferior spinous processes, respectively;

wherein said generating measurement data comprises generating measurement data indicative of strain experienced by said first interspinous implant and transmitting said measurement data from said first interspinous implant;
wherein said disposing a spinal stabilizer between the spinous processes comprises unmating said sensor module from said receiver body and mating a second module to said receiver body; and
wherein said spinal stabilizer has a stiffness different than said first interspinous implant.

12. The method of claim 11 wherein said disposing a spinal stabilizer between the spinous processes comprises unmating said sensor module from said receiver body and mating a second module to said receiver body during a subsequent surgical procedure.

13. A method of spacing an upper spinous process relative to a lower spinous process, comprising:
creating a first incision in a human body during a first surgical procedure;
inserting a first implant between the spinous processes during the first surgical procedure; wherein the first implant comprises an upper saddle, a lower saddle, and a sensor disposed between the upper and lower saddles;
wherein inserting the first implant comprises inserting the first implant between the spinous processes such that the upper saddle receives the upper spinous process, the lower saddle receives the lower spinous process, and the sensor is disposed between the upper and lower spinous processes;
closing the first incision;
generating measurement data with the sensor indicative of a mechanical strain applied by the spinous processes and transmitting the measurement data from the first implant while the first implant is disposed between the spinous processes;
thereafter, creating a second incision in the human body during a subsequent second surgical procedure;
removing a first insert from a receiver body of the first implant during the subsequent second surgical procedure;
selecting a second insert based on the measurement data;
inserting the second insert in the receiver body so as to be disposed between the spinous processes during the subsequent second surgical procedure;
thereafter, closing the second incision.

14. The method of claim 13 wherein selecting said second insert comprises selecting said second insert based on said measurement data and a material property of said second insert.

15. The method of claim 14 wherein the material property of the second spinal implant is a stiffness thereof.

16. The method of claim 14 wherein the material property of the second implant is a flexural modulus thereof.

17. The method of claim 13 wherein inserting the first implant comprises inserting the first implant such that the sensor extends through a sagittal plane defined by the spinous processes.

* * * * *